(12) United States Patent
Bienenstock

(10) Patent No.: US 10,463,335 B2
(45) Date of Patent: Nov. 5, 2019

(54) SINGLE PHOTON EMISSION COMPUTED TOMOGRAPHY IMAGING METHOD

(71) Applicant: Elazar A. Bienenstock, Toronto (CA)

(72) Inventor: Elazar A. Bienenstock, Toronto (CA)

( * ) Notice: Subject to any disclaimer, the term of this patent is extended or adjusted under 35 U.S.C. 154(b) by 562 days.

(21) Appl. No.: 14/896,268

(22) PCT Filed: Jun. 9, 2014

(86) PCT No.: PCT/CA2014/000529
§ 371 (c)(1),
(2) Date: Dec. 4, 2015

(87) PCT Pub. No.: WO2014/194412
PCT Pub. Date: Dec. 11, 2014

(65) Prior Publication Data
US 2016/0128662 A1    May 12, 2016

(30) Foreign Application Priority Data

Jun. 7, 2013 (CA) ..................... 2818239

(51) Int. Cl.
*A61B 6/00* (2006.01)
*A61B 6/03* (2006.01)

(52) U.S. Cl.
CPC .............. *A61B 6/507* (2013.01); *A61B 6/037* (2013.01); *A61B 6/503* (2013.01)

(58) Field of Classification Search
CPC .......... A61B 6/037; A61B 6/503; A61B 6/507
See application file for complete search history.

(56) References Cited

U.S. PATENT DOCUMENTS

| | | |
|---|---|---|
| 8,000,773 B2 | 8/2011 | Rousso et al. |
| 2010/0104505 A1 | 4/2010 | O'Connor |
| 2012/0275657 A1 | 11/2012 | Kolthammer et al. |

FOREIGN PATENT DOCUMENTS

WO    2011070465 A2    6/2011

OTHER PUBLICATIONS

Finucane et al., Quantitative Accuracy of Low-Count SPECT Imaging in Phantom and In Vivo Mouse Studies, International Journal of Molecular Imaging, vol. 2011, Article ID 197381, Published online Mar. 16, 2011.*
DePuey et al., Updated Imaging Guidelines for Nuclear Cardiology Procedures Part 1, Journal of Nuclear Cardiology, vol. 8, No. 1 Jan./Feb. 2001.*

* cited by examiner

*Primary Examiner* — Bo Joseph Peng
(74) *Attorney, Agent, or Firm* — The Webb Law Firm

(57) ABSTRACT

A SPECT diagnostic method of performing myocardial perfusion imaging on a patient, the method including (A) commencing a myocardial perfusion diagnostic scan; (B) during the scan, determining the photon count rate; (C) using the photon count rate and a predetermined total photon count target, determining a scan duration time; (D) terminating the diagnostic scan when the scan duration time elapses.

12 Claims, No Drawings

SINGLE PHOTON EMISSION COMPUTED TOMOGRAPHY IMAGING METHOD

CROSS-REFERENCE TO RELATED APPLICATIONS

This application is the United States national phase of International Application No. PCT/CA2014/000529 filed Jun. 9, 2014, and claims priority to Canadian Patent Application No. 2,818,239 filed Jun. 7, 2013, the disclosures of which are hereby incorporated in their entirety by reference.

FIELD OF THE INVENTION

This invention is directed to the field of Single Photon Emission Computed Tomography.

BACKGROUND OF THE INVENTION

Nuclear medicine is a field of medicine concerned with the use of radiation for diagnostic purposes. Single Photon Emission Computed Tomography (referred to in this specification as "SPECT"), a branch of nuclear medicine, involves directly measuring gamma rays emitted by radionuclides administered to a patient to produce slice-like images of the patient. "Tomography" refers to the production of slice-like images, or tomograms. Computerized Tomography (CT) refers to the use of computer processing to derive the tomogram.

Typically, in SPECT procedures, radiopharmaceuticals (otherwise known as radioactive tracers or radiotracers) are administered to patients. Radiopharmaceuticals are generally compounds consisting of radionuclides (i.e. radiation-emitting atoms), combined with pharmaceuticals or other chemical compounds. In some cases, such as with Thallium-201, the same particle is simultaneously the radionuclide and pharmaceutical. Unlike positron emission tomography (PET), which uses small radionuclides with half-lives of just over a minute to under 2 hours, SPECT involves the use of radionuclides whose half-life is several hours to days long, long enough to clinically localize or become fixed in specific organs or cellular receptors. In these circumstances, it is possible to acquire important diagnostic information by obtaining images created from the radiation emitted by the radiopharmaceutical.

One frequently-performed SPECT diagnostic procedure is myocardial perfusion imaging (MPI). Approximately ten million such scans are performed in the U.S. annually. For MPI, the patient is injected with a radioactive tracer which collects in, and becomes fixed in, the heart muscle. The localization of the tracer within the heart is dictated by the blood flow through the coronary arteries. These are the blood vessels that supply blood directly to the heart muscle, the myocardium. Therefore, MPI provides important information about the blood flow through the coronary arteries to the heart muscle. Thus, MPI can be used to diagnose serious and potentially fatal heart conditions such as coronary artery disease.

In prior art configurations, the time used to complete a SPECT scan is typically fixed. The camera being used is typically configured to operate for a predetermined period of time receiving photons from the patient. This is the case, for example, with conventional Anger-type cameras, as well as the GE™ 530c, a newer CZT camera. The Spectrum Dynamics D-SPECT™ camera uses a pre-scan performed prior to the diagnostic scan to determine the length of the diagnostic scan. Thus, scans done according to both these methods (most often the former) can be unduly long, causing undesirable delay both systemically and to individual patients.

SUMMARY OF THE INVENTION

Therefore, what is desired in an aspect of the invention is a SPECT imaging method that provides a means to reduce average SPECT scan time as compared with at least one of the prior art methods referred to above. According an aspect of the invention, there is provided a SPECT diagnostic method of performing myocardial perfusion imaging on a patient, the method comprising the steps of:

(A) commencing a myocardial perfusion diagnostic scan;
(B) during the scan, determining the photon count rate;
(C) using the photon count rate and a predetermined total photon count target, determining a scan duration time;
(D) terminating the diagnostic scan when the scan duration time elapses.

In another aspect of the invention, there is provided a SPECT diagnostic method of performing myocardial perfusion imaging on a patient, the method comprising the steps of:

(A) determining a volume of a left ventricle of the patient;
(B) determining the photon count rate;
(C) commencing a myocardial perfusion diagnostic scan;
(D) using the volume, the photon count rate and a predetermined photon count density, determining a scan duration time;
(E) terminating the diagnostic scan when the scan duration time elapses.

DETAILED DESCRIPTION OF THE PREFERRED EMBODIMENTS

In SPECT imaging, obtaining an adequate diagnostic imaging requires enough photon counts to produce a sufficiently clear, statistically valid, image. Thus, the higher the photon count rate (i.e. the rate at which the camera receives photons used to construct the diagnostic image), the more quickly, in theory, a diagnostically adequate image can be obtained.

There are a number of factors that affect the photon count rate. Some of these relate to the patient. For example, soft tissue attenuation reduces count rate so that, all other things being equal, the photon count rate for an obese patient having a BMI of 40 would be significantly lower than for a patient having a BMI of 20.

Also, Compton scatter blurs the image, requiring a higher number of photon counts to compensate for the blurring effect. Compton scatter is essentially the deflection of photons by body tissue, which causes the camera to misplace the origin of the deflected photons.

Also, the volume of distribution, i.e. the scanned volume (for example, in MPI, the volume of the left ventricle) also affects photon count rates.

Other relevant factors include intentional and unintentional variations in the amount of radiotracer administered and variation among patients in the proportion of the radiotracer dose which fixes in the relevant organ.

Those skilled in the art will appreciate that photon count rate is also affected by the type of camera used for the SPECT scan, and the positioning of the camera. The radiotracer emits photons in all directions, but only a small percentage of those will reach the camera at an angle that allows them to be used as part of the scan.

Other factors will be known to those skilled in the art.

Given the various factors that affect count rate, the time needed to obtain a diagnostically valid SPECT image will vary from patient to patient, camera to camera, and scan to scan. Historically, however, cameras have generally been programmed to scan for a particular period of time without regard to the number of photon counts.

This approach produces some undesirable results. Although the scan times are selected to ensure that the vast majority of scans produce diagnostically valid images, there are cases where the number of photon counts is too low and the scan must be repeated.

More often, however, because the scan times are preselected to ensure that almost all scans are diagnostically valid, most scans actually take longer than they should. In addition to decreasing patient convenience and comfort and increasing hearth-care costs, longer scan times increase the likelihood of patient motion, which can ruin scans. Alternatively, the scans that could be done more quickly might instead be done over the same length of time, but with a lower radiation dose (that would reduce the photon count rate).

By contrast, in one aspect of the present invention, the photon count rate (i.e. the number of photons reaching the camera to be included in the scan, per unit time), together with a predetermined total photon count target, are used to determine the scan duration time (i.e. the time period beginning when the scan begins, and ending when it ends). In other words, once the desired total number of photon counts is reached (this is a predetermined number), the scan terminates. Meanwhile, the total photon count target may be predetermined with reference to the number of photon counts required to produce a diagnostically valid SPECT scan.

In another aspect of the invention, there is a predetermined target number of photon counts per unit of scanned volume (also referred to as photon count density). Scanned volume is the volume of the tissue being scanned. In MPI scans, for example, the scanned volume is the volume of the left ventricle portion of the myocardium. In this aspect of the invention, the scan duration time is determined by determining the photon count rate, and using the predetermined photon count density, the scanned volume and the photon count rate to determine the scan duration time.

The preferred embodiment of the invention will be described with reference to MPI. However, it will be appreciated that at least one embodiment of the method described here may be applied to other scanned volumes, organs, tissues or other body parts that can be subjected to SPECT imaging.

Preferably, to save time, the calculation of the scan duration time will take place after the diagnostic scan commences. The photon count rate is the number of photons making up the diagnostic image being received by the camera, per unit time. Thus, in a typical MPI diagnostic scan, the diagnostic scan is commenced. During the scan (when photons that form part of the diagnostic image are being received by the camera), the photon count rate is also determined. This is both possible and beneficial because as the camera receives photons emitted by the radiotracer, it can use them for the diagnostic image, and also count them and determine their rate of arrival.

Though much less preferred, it is possible to determine the photon count rate before the diagnostic scan commences. However, such an approach would add to the diagnostic scan the time needed to separately ascertain the photon count rate. For this reason it is most preferred to ascertain the photon count rate concurrently with the diagnostic scan being performed.

In one aspect of the invention, there is a predetermined photon count density that is desired. Photon count density is the total number of photons received by the camera during the scan, divided by the scanned volume (e.g. the volume of the left ventricle). The photon count density is relevant because the size of the scanned volume (e.g. the left ventricle) affects the number of photon counts needed to obtain a diagnostically valid image. For example, a larger left ventricle requires a higher number of photon counts for a diagnostically valid image than does a smaller left ventricle, all other things being equal.

To determine the scan duration time, the scanned volume (e.g. the volume of the left ventricle) is determined. Typically, this is achieved in one of two ways. One is that the SPECT technician manually identifies the scanned volume (e.g. the boundaries of the left ventricle) to the camera using the low-count image that was obtained since the commencement of the scan. The second method is automatic computerized threshold segmentation. This can be done because, even with a count-poor image that is diagnostically suboptimal, the contours of the volume of distribution are reasonably well defined. The camera and its associated computer hardware and software then estimate the scanned volume (e.g. the volume of the left ventricular myocardium). As such, it is possible to program the camera with known numerical and statistical methods that permit the camera to estimate the scanned volume (e.g. the left ventricular myocardium).

Using the low-count image referred to above to estimate scanned volume requires some adaptation depending on the camera being used. Using a GE™ D530c camera, which acquires images from all angles at once, a partial image saved any time during the scan, though possibly count-poor, can be reconstructed and used to identify the scanned volume. By contrast, as described below, with conventional Anger type cameras, the camera moves across an angular range at least 180 degrees taking multiple planar images used to produce the final diagnostic image. A partial image from an Anger camera used to estimate scanned volume, in addition to being count-poor, would have incomplete angular sampling (i.e. less than one 180 degree rotation), and could not be reconstructed into a SPECT image. Further study may indicate that it is possible to estimate LV count rate from a set of planar images, in which case planar images would be used to estimate scan-time without reconstruction. This would obviate the need for multiple accelerated gantry rotations when applying this method to Anger SPECT as will be described below.

Determining the scan duration time involves multiplying the scanned volume (SV) by the predetermined photon count density (PCS) to obtain the desired total photon counts (TPC), and dividing the TPC by the photon count rate (PCR) to obtain the scan duration time (SDT). Thus, $$SDT=(SV \times PCS)/PCR$$

In another aspect of the invention, a predetermined total photon count (TOTPC) number is used to calculate the scan duration time, rather than a predetermined PCS. In this other aspect, $$SDT=TOTPC/PCR$$

In this other aspect, scanned volume is not used to calculate the scan duration time. This approach has the benefit of being simpler, and in cases where the volume is being estimated using manual means, labour-saving. Generally, in cases where the size of the scanned volume is less likely to have a pronounced effect on the number of counts required for a diagnostically valid image, the upsides of this approach would be greater relative to the downsides than in other cases.

The scan duration time begins at the commencement of the SPECT scan (e.g. the myocardial perfusion diagnostic scan). Once the scan duration time has ended, the scan is terminated. It will be appreciated that in light of the many factors that affect count rate, the scan duration time will generally be different for different patients.

This will preferably produce one or more of the following benefits. First, each patient will be required to remain under the camera only as long as it takes to produce an image that is adequate for diagnostic purposes.

Second, the patient is kept under the camera until enough photon counts are received to create an image that is adequate diagnostically, with the result that the patient is far less likely than under prior art methods to require re-attendance for a second scan.

Third, this method can provide increased flexibility in one or more aspects of the SPECT imaging process. For example, a lower radiation dose can be administered, resulting in a longer scan duration time, or a larger dose resulting in a shorter scan duration time, with confidence that the image will comprise enough photon counts. Alternatively, there may be some situations in which a very clear and detailed image is required, and others in which the image need not be so clear and detailed. The present method allows for the scan duration time to be adjusted to yield the image quality that is required in the particular circumstances.

Conventional Anger-type cameras typically operate by having a gantry move the camera over about 180 degrees, during which the gantry takes about 60 planar images that are used to construct the final diagnostic image. The gantry pauses at each position to take each planar image. The time for the entire gantry rotation is the time that the camera is paused at the imaging positions, plus the time the camera takes to move from each position to the next. Since any particular Anger-type camera will have a predetermined speed of movement, the simplest way to change the scan time for a particular camera is to change the amount of time the camera pauses at each position.

Since all of the planar images are used to construct the final image, it is undesirable to end the scan before the full set of planar images has been obtained. Thus, for an Anger-type camera, the scan duration time can be determined as follows.

Instead of having the camera complete one 180-degree rotation, the Anger-type camera can be configured to go through more than one, and preferably three, such rotations. The time of each rotation would be reduced accordingly by reducing the duration of the pause at each imaging position. During each rotation, the cameras would image from the same set of positions (typically about 60 scans every 3 degrees) and the three data sets obtained at each position would be merged to produce the planar image corresponding to each position. Known techniques can then be employed to use the set of planar images (typically about 60 of them) to create the diagnostic image. Accordingly, all three rotations are part of the diagnostic scan.

Preferably, the first of the three gantry rotations will be timed to permit the camera to obtain data to determine the photon count rate, while simultaneously receiving photons for the planar images that will be used to construct the diagnostic image. During the second gantry rotation, while the camera continues to take the planar images to be used to construct the diagnostic images, the camera's associated hardware and software can determine the photon count rate and scanned volume (e.g. left ventriclar myocardial volume). During the second rotation, the scan duration time would also be determined.

Preferably, the time taken for each of the first and second gantry rotations is as close as possible to the minimum time required for the camera to perform the required data collection and calculations just described. Once the scan duration time is determined, the time of the third and final gantry rotation is determined so that the diagnostic scan, which includes all three gantry rotations, ends when the scan duration time elapses.

Thus, for example, if each of the first two rotations is two minutes in length, and the scan duration time is determined to be 9.5 minutes (a typical scan time for conventional Anger-type cameras), then the time for the third rotation would be set at 5.5 minutes. Newer and faster reconstruction algorithms used with Anger cameras (e.g. UltraSpect™) have reduced a typical scan time to about 4 minutes. In such a case, it would be preferable to reduce each of the first to rotations to a scan time of 30-45 seconds. Alternatively, instead of decreasing the pause time for each gantry position, the angular steps can be increased. Increasing angular sampling steps from 3 to 6 degrees decreases the number of steps by half and has the same effect on gantry rotation time as decreasing step time in half.

It will be appreciated that the method may be implemented using a conventional Anger-type camera with two or more rotations, with the first rotation being used to acquire data regarding photon count rate, and the time duration of a subsequent rotation being determined and adjusted once the scan duration time has been calculated.

The current Spectrum Dynamics D-SPECT™ CZT camera, which takes images from different angles and then uses reconstruction algorithms to create the diagnostic image, is configured to conduct a non-diagnostic pre-scan to determine the photon count rate. Once that is determined, the diagnostic scan commences, and continues until the desired total number of photon counts is reached. A downside of this current configuration is that time is spent on a pre-scan that is not part of the diagnostic scan. Also, this camera does not use the scanned volume (e.g. left ventricle volume) as a factor in determining the scan duration time. By contrast, the present invention comprehends commencing the diagnostic scan, and using the photons that are received as part of the diagnostic scan both to determine photon count rate (used for determining scan duration time), and for creating the diagnostic image. It also, in one aspect, comprehends using the scanned myocardial volume as a factor in determining the scan duration time.

The GE™ D530c CZT camera acquires all angles simultaneously, and does not currently use either the photon count rate or the scanned volume to determine the scan duration time. However, because it acquires all angles at once, it is well-suited, with appropriate programming, to carrying out the present invention. Specifically, because it acquires all angles at once, it can be programmed to produce a partial SPECT image for determining scanned volume, and to determine photon count rate, all at any point after the commencement of the diagnostic scan. This is to be contrasted with Anger-type cameras which view one angle at a time, and which therefore require more complicated workarounds for executing the present invention, as described above.

In a further aspect of the invention, there is provided a method of comparing the efficiency of a first SPECT camera with the efficiency of a second. It will be appreciated that the time required to obtain a valid diagnostic SPECT image will vary with the size of the radiation dose administered to the patient. With a higher dose of radiotracer (i.e. more radioactivity), the image can be acquired more quickly, and with less, it would be acquired more slowly.

SPECT cameras can therefore be compared by how much scanning time is required for at any particular level of radioactivity. One way to express this efficiency level is to multiply radioactivity units (which measure the number of disintegrations per unit time) by the number of units of time required to scan to obtain a diagnostically valid image. A common unit of radiation is the MegaBecquerel (MBq), which is one million Becquerel, the SI unit of radioactivity (seconds$^{-1}$). Time may be measured in seconds, resulting in a MegaBecquerel-Second Product (MSP) that is technically dimensionless. The MSP shows the efficiency of a camera because it indicates the absolute number of disintegrations that are required to produce a diagnostically valid SPECT image.

It will be appreciated that other measures of radioactivity (e.g. mCi) and time may be used. Preferably, these measures will be chosen so that the resulting Product will indicate the absolute number of disintegrations needed to produce a diagnostically valid image.

It will be appreciated that, to use this method of comparing camera efficiencies, it is necessary to define what constitutes a diagnostically valid image in a consistent way for the cameras being compared. This definition may be a total photon count number, a specific photon count density, or some other definition. The total number of counts or the count density can be different for cameras with different geometries and must therefore be determined, estimated or otherwise agreed on, independently for each camera system being compared. In other words, for two cameras having different geometries, different photon count totals or densities may be requires to achieve equal image quality. In comparing efficiencies, the image quality must be the same for both cameras, and not necessarily the count totals or count densities.

To perform the comparison, at least one scan is performed by the first camera using a known level of radioactivity. The time elapsed in obtaining a diagnostically valid image is determined, and the efficiency level (preferably MSP) is calculated by multiplying the radioactivity (preferably in MBq) by the time (preferably in seconds). If more than one scan is done for the first camera, and different efficiency levels are obtained, an overall efficiency level can be obtained by averaging the individual MSPs from the individual scans. It will be appreciated that the various different known types of averages (e.g. median, mean, mode) may be used, depending on the type of comparison to be made.

The same process that is conducted for the first camera is conducted for the second, and resulting efficiency level is compared with that of the first camera. The scans used by the first and second cameras should be equivalent, meaning that they are imaging the same organ or the like. It will be appreciated that the lower the MSP, the more efficient the camera.

It will further be appreciated that that, currently, camera vendors may recommend to SPECT laboratory that they use a particular scan-time for a particular dosage level of radiation. However, using MSP, the vendor can simply identify to the vendor the MSP of the camera, and the user would be free to choose radioactivity and scanning time that meeting this specification.

While the foregoing preferred embodiments of the present invention have been set forth in considerable detail for the purpose of making a complete disclosure of the invention, it will be apparent to those skilled in the art that other embodiments described herein are comprehended by the broad scope of the invention as defined in the attached claims.

The invention claimed is:

1. A SPECT diagnostic method of performing myocardial perfusion imaging on a patient, the method comprising the steps of:
   (A) commencing a myocardial perfusion diagnostic scan of a patient using a SPECT camera, wherein the SPECT camera comprises an Anger-type SPECT camera comprising first, second, and third gantry rotations;
   (B) during the myocardial perfusion diagnostic scan of the patient, determining a photon count rate comprising a rate at which the Anger-type SPECT camera receives photons used to construct a myocardial perfusion image, wherein the photon count rate is determined during the first gantry rotation;
   (C) using the photon count rate and a predetermined total photon count target, determining a scan duration time for said myocardial perfusion diagnostic scan of the patient during the myocardial perfusion diagnostic scan, wherein the scan duration time is determined during the second gantry rotation; and
   (D) terminating the myocardial perfusion diagnostic scan when the scan duration time elapses.

2. The method as claimed in claim 1, wherein step (C) comprises dividing the predetermined total photon count target by the photon count rate to obtain the scan duration time.

3. The method as claimed in claim 1, wherein step (D) comprises terminating the third gantry rotation when the scan duration time elapses.

4. A SPECT diagnostic method of performing myocardial perfusion imaging on a patient, the method comprising the steps of:
   (A) determining a volume of muscle tissue of a left ventricle portion of a heart of the patient;
   (B) determining a photon count rate comprising a rate at which a SPECT camera receives photons used to construct a myocardial perfusion image;
   (C) commencing a myocardial perfusion diagnostic scan of the patient using the SPECT camera;
   (D) during the myocardial perfusion diagnostic scan of the patient and using the volume, the photon count rate and a predetermined photon count density, determining a scan duration time for said myocardial perfusion diagnostic scan of the patient; and
   (E) terminating the myocardial perfusion diagnostic scan of the patient when the scan duration time elapses.

5. The method as claimed in claim 4, wherein step (D) comprises multiplying the photon count density by the volume to obtain a desired total photon count, and dividing the desired total photon count by the photon count rate to obtain the scan duration time.

6. The method as claimed in claim 4, further comprising identifying the left ventricle.

7. A SPECT diagnostic method of performing myocardial perfusion imaging on a patient, the method comprising the steps of:
   commencing a myocardial perfusion diagnostic scan of a patient using a SPECT camera;
   during the myocardial perfusion diagnostic scan of the patient, determining a photon count rate comprising a rate at which the SPECT camera receives photons used to construct a myocardial perfusion image;

during the myocardial perfusion diagnostic scan of the patient and using a volume of muscle tissue of a left ventricle portion of a heart of the patient, the photon count rate, and a predetermined photon count density, determining a scan duration time for the myocardial perfusion diagnostic scan of the patient; and terminating the myocardial perfusion diagnostic scan of the patient when the scan duration time elapses.

8. The SPECT diagnostic method of claim 7, wherein commencing the myocardial perfusion diagnostic scan of the patient using the SPECT camera comprises:

commencing the myocardial perfusion diagnostic scan of the patient using an Anger-type SPECT camera, wherein the Anger-type SPECT camera comprises one or more gantry rotations; and wherein determining the photon count rate comprising the rate at which the SPECT camera receives photons used to construct the myocardial perfusion image comprising:

during the myocardial perfusion diagnostic scan of the patient, determining the photon count rate comprising the rate at which the Anger-type SPECT camera receives photons used to construct the myocardial perfusion image.

9. The SPECT diagnostic method of claim 7, wherein the SPECT camera comprises an Anger-type SPECT camera that comprises one or more gantry rotations, and wherein determining the scan duration time for the myocardial perfusion diagnostic scan of the patient comprises:

during the myocardial perfusion diagnostic scan of the patient and using the volume of muscle tissue of the left ventricle portion of the heart of the patient, the photon count rate, and a predetermined photon count density, determining the scan duration time for the myocardial perfusion diagnostic scan of the patient during the one or more gantry rotations.

10. The SPECT diagnostic method of claim 9, wherein the photon count rate is determined during a first gantry rotation of the one or more gantry rotations and the scan duration time for said myocardial perfusion diagnostic scan is determined during a second gantry rotation of the one or more gantry rotations.

11. The SPECT diagnostic method of claim 7, further comprising:

determining the volume of muscle tissue of the left ventricle portion of the heart of the patient during the myocardial perfusion diagnostic scan.

12. The SPECT diagnostic method of claim 7, wherein determining the scan duration time for the myocardial perfusion diagnostic scan of the patient comprises:

multiplying the photon count density by the volume of muscle tissue of the left ventricle portion of the heart of the patient to obtain a desired total photon count; and dividing the desired total photon count by the photon count rate to obtain the scan duration time.

* * * * *

UNITED STATES PATENT AND TRADEMARK OFFICE
CERTIFICATE OF CORRECTION

PATENT NO. : 10,463,335 B2
APPLICATION NO. : 14/896268
DATED : November 5, 2019
INVENTOR(S) : Elazar A. Bienenstock Page 1 of 1

It is certified that error appears in the above-identified patent and that said Letters Patent is hereby corrected as shown below:

On the Title Page

Column 2, Line 3, delete "mycocardial" and insert -- myocardial --

Signed and Sealed this
Eleventh Day of February, 2020

Andrei Iancu
*Director of the United States Patent and Trademark Office*